United States Patent [19]
Hashimoto et al.

[11] Patent Number: 5,082,974
[45] Date of Patent: Jan. 21, 1992

[54] 3-HALOGENO-2,3-DIPHENYLACRYLALDE-HYDE DERIVATIVES, PROCESS FOR PREPARING THE SAME AND A PHARMACEUTICAL COMPOSITION FOR TREATING HYPERLIPIDEMI

[75] Inventors: Kinji Hashimoto; Makoto Inoue; Junichi Minamikawa, all of Naruto, Japan

[73] Assignee: Otsuka Pharaceutical Factory, Inc., Naruto, Japan

[21] Appl. No.: 623,404

[22] PCT Filed: Apr. 23, 1990

[86] PCT No.: PCT/JP90/00526
  § 371 Date: Dec. 10, 1990
  § 102(e) Date: Dec. 10, 1990

[87] PCT Pub. No.: WO90/12786
  PCT Pub. Date: Nov. 1, 1990

[30] Foreign Application Priority Data
  Apr. 24, 1989 [JP] Japan .................. 1-103981

[51] Int. Cl.$^5$ .................. C07C 317/14; C07C 317/22
[52] U.S. Cl. .................. 568/41; 568/27; 568/37; 568/38
[58] Field of Search .................. 568/37, 38, 41, 27

[56] References Cited
U.S. PATENT DOCUMENTS
4,324,628 4/1982 Avar et al. .................. 568/37

Primary Examiner—Warren B. Lone
Attorney, Agent, or Firm—Armstrong, Nikaido, Marmelstein, Kubovcik & Murray

[57] ABSTRACT

3-Haolgeno-2,3-diphenylacrylaldehyde derivatives represented by the formula

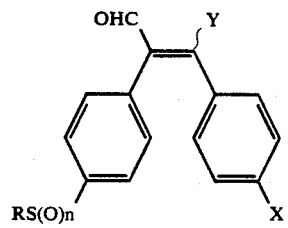

wherein R is an alkyl group having 1 to 6 carbon atoms, X and Y each represent a halogen atom, and n is 0, 1, or 2, a process for preparing the derivatives, a medicament for preventing and treating hyperlipidemia containing a pharmacologically effective amount of the derivative, and a method for preventing or treating hyperlipidemia using the medicament.

5 Claims, No Drawings

3-HALOGENO-2,3-DIPHENYLACRYLALDEHYDE DERIVATIVES, PROCESS FOR PREPARING THE SAME AND A PHARMACEUTICAL COMPOSITION FOR TREATING HYPERLIPIDEMI

TECHNICAL FIELD

The present invention relates to novel 3-halogeno-2,3-diphenylacrylaldehyde derivatives, a process for preparing the derivatives and a pharmaceutical composition containing such derivative for treating hyperlipidemia. The derivatives are also useful as synthetic intermediates for diphenylthiophene derivatives usable as an anti-inflammatory agent.

PRIOR ART AND PROBLEMS THEREOF

An object of the present invention is to provide novel compounds useful not only as synthetic intermediates for an anti-inflammatory agent, but as a medicament such as an agent for treating hyperlipidemia.

Another object of the invention is to provide a process for mass production of the compounds.

A further object of the invention is to provide a novel medicament for treating hyperlipidemia and a method of treating and preventing hyperlipidemia.

DISCLOSURE OF THE INVENTION

According to the present invention, there are provided 3-halogeno-2,3-diphenylacrylaldehyde derivatives represented by the following general formula [1]

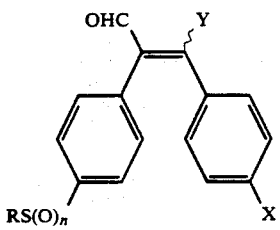

wherein R is an alkyl group having 1 to 6 carbon atoms, X and Y each represent a halogen atom, and n is 0, 1 or 2, and a process for preparing the derivatives.

We conducted extensive research and successfully prepared the compounds of the general formula [1]. Our findings were that the compounds are useful as intermediates for synthesizing diphenylthiophene derivatives represented by the formula [7] given hereinafter and usable as an anti-inflammatory agent, and that the compounds per se have an activity of lowering the concentration of lipids and are thus useful for treating or preventing, e.g., hyperlipidemia such as hypercholesterolemia, hypertriglyceridemia, hyperphospholipidemia, hyper-free fatty acidemia and the like. The present invention has been accomplished based on these novel findings.

Specific examples of the alkyl groups of 1 to 6 carbon atoms represented by R are methyl, ethyl, propyl, isopropyl, butyl, t-butyl, pentyl, hexyl and like straight- or branched-chain alkyl groups. Examples of the halogen atoms represented by X, Y or Z include fluorine, chlorine, bromine and iodine.

The compounds represented by the formula [1] wherein X is a fluorine atom and Y is a chlorine atom are more preferable.

The derivatives of the present invention can be prepared by various processes, more specifically by the process as illustrated below in Reaction Scheme-1.

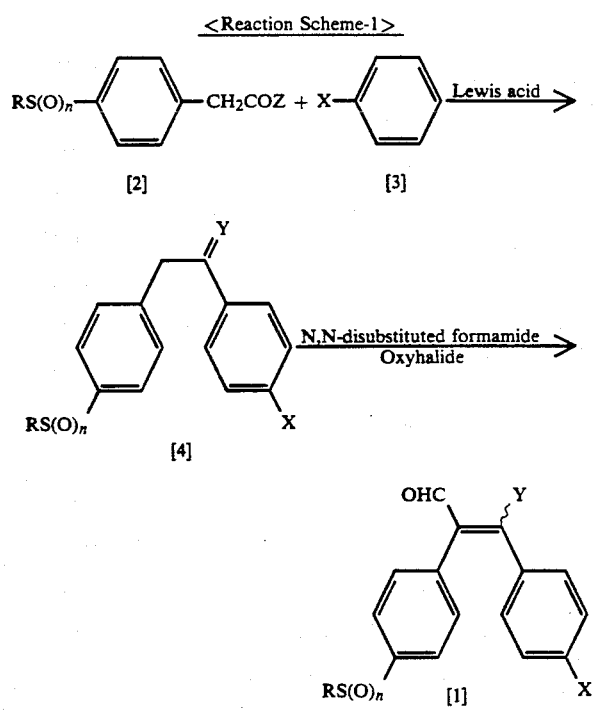

In the foregoing formulae, R, X, Y and n are as defined above, and Z is a halogen atom.

The phenylacetyl halide derivative [2] used as the starting material in Reaction Scheme-1 can be prepared substantially quantitatively by reacting the corresponding phenylacetic acid derivative with a nucleophilic halogenating agent such as thionyl chloride, thionyl bromide, phosphorus pentachloride, phosphorus trichloride, oxalyl chloride or the like.

In Reaction Scheme-1, the reaction of the phenylacetyl halide derivative [2] with the halogenobenzene derivative [3] can be conducted usually with an ordinary Lewis acid in the presence or absence of a suitable solvent. In particular, the halogenobenzene derivative [3] used in the reaction can also serve as a solvent and can be readily recovered after the reaction. In this case, it is preferable to effect the reaction without addition of a solvent. However, the reaction may be carried out using common inert organic solvents such as dichloromethane, 1,2-dichloroethane, carbon disulfide and the like. Illustrative of useful Lewis acids are various kinds of those commonly used, such as aluminum chloride, titanium tetrachloride, ferric chloride, zinc chloride, boron trifluoride etherate and the like. The kind and the amount of the Lewis acid used can be suitably determined depending on the reactivity, selectivity and the like. The Lewis acid is usually used in an amount of about 1 to about 5 moles, preferably about 1 to about 2 moles, per mole of the phenylacetyl halide derivative [2]. A suitable reaction temperature is in the range of about $-10°$ to about $100°$ C. The reaction can be conducted by any of the procedures as set out below in 1 and 2.

1. The phenylacetyl halide derivative [2] is added to a mixture of the halogenobenzene derivative [3] and the Lewis acid; or 2. The Lewis acid is added to a mixture of the halogenobenzene derivative [3] and the phenylacetyl halide derivative [2].

In any of these procedures, the reaction is completed in about 3 to about 30 hours.

After completion of the reaction, the desired desoxybenzoin derivative [4] can be separated from the reaction mixture by a usual method, as by adding the reaction mixture to an aqueous solution of a dilute inorganic acid to decompose the mixture, collecting the resulting solids by filtration, dissolving the solids in an appropriate organic solvent, washing the solution and then removing the organic solvent. The unreacted halogenobenzene derivative [3] can be recovered by separating the organic layer from the filtrate, followed by distillation.

The desoxybenzoin derivative [4] thus obtained can be converted into the desired derivative [1] according to the present invention by being treated with N,N-disubstituted formamide and an oxyhalide. While a solvent need not be used in this reaction because of the presence of the N,N-disubstituted formamide capable of acting as a solvent, an anhydrous inert organic solvent may be used such as chloroform, toluene, benzene, 1,2-dichloroethane and the like.

Examples of the N,N-disubstituted formamide used hereinabove include various kinds of those known, such as N,N-dimethylformamide, N,N-diethylformamide, N-methyl-N-phenylformamide and the like. Representative of the oxyhalide are various kinds of conventional ones, such as phosphorus oxychloride, thionyl chloride, phosgene and the like among which phosphorus oxychloride is preferable to use. The amount of the oxyhalide used is usually about 1 to about 10 moles, preferably about 3 to about 4 moles, per mole of the desoxybenzoin derivative [4]. A suitable reaction temperature is about 0° to about 150° C.

The derivatives [1] according to the present invention can be separated from the reaction mixture obtained above by the conventional method, for example a method comprising adding the reaction mixture to ice water to hydrolyze the mixture and extracting the hydrolyzate with an appropriate solvent. The obtained derivatives [1] can be purified by the conventional purification method such as a solvent extraction method, recrystallization, column chromatography or the like.

The process for preparing the derivatives [1] of the invention as illustrated above in Reaction Scheme-1 is advantageous in terms of the following items and is especially preferred in that the process can conduct mass production of the derivatives.

1. The starting materials and reagents to be used are inexpensive and easily available.
2. Substantially no hazard is involved in handling the reagents and intermediates for use in the reaction.
3. The desired products of high purity can be obtained in a high yield with satisfactory reproducibility.

The 3-halogeno-2,3-diphenylacrylaldehyde derivatives [1] according to the invention are useful as synthetic intermediates of diphenylthiophene derivatives [7] usable as an anti-inflammatory agent (e.g., please refer to Unexamined Japanese Patent Publication No. 159489/1983). The diphenylthiophene derivatives can be prepared from the derivatives [1] of the invention by, for example, a process as illustrated below in Reaction Scheme-2.

<Reaction Scheme-2>

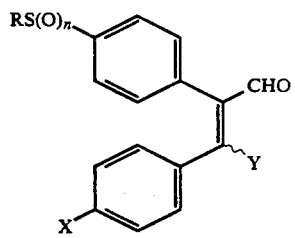

[1]

↓ HSCH₂COOH

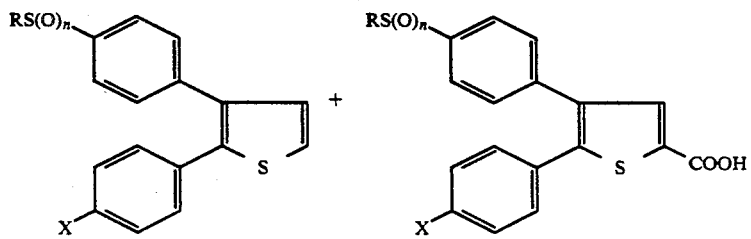

[5]    [6]
  ↘  Heating  ↙

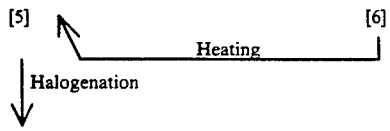

↓ Halogenation

<Reaction Scheme-2>

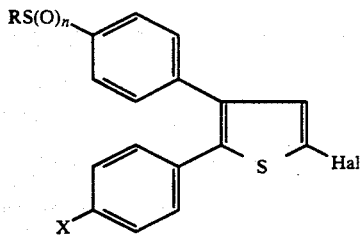

[7]

In the above formulae, R, X, Y and n are as defined above, and Hal is a halogen atom.

In accordance with the process as shown above in Reaction Scheme-2, the derivative [1] of the invention and a thioglycolic acid are first subjected to condensation reaction to give a compound [5]. The condensation reaction can be conducted in an inert basic solvent such as pyridine, picoline, lutidine, collidine or the like. The reaction temperature is about 0° to about 160° C. The proportions of the both starting materials are about 1 to about 1.5 moles of the thioglycolic acid per mole of the derivative [1] of the invention. The reaction is completed usually in about 1 to about 8 hours. In the reaction system for the condensation, a common organic amine such as triethylamine, N,N-diisopropylethylamine or the like is preferably used as an acid binder in an appropriate amount, usually in an amount of about 1 to about 3 moles per mole of the derivative of the invention.

Although the condensation reaction gives the compound [6] as a by-product, the compound [6] thus formed can be readily converted into the compound [5] as by heating in the presence of copper powder to cause decarboxylation.

According to Reaction Scheme-2, the compound [5] thus obtained is halogenated using an electrophilic halogenating agent to prepare the desired compound [7]. The halogenation reaction can be performed as described below in the same manner as e.g., the method disclosed in the aforementioned Unexamined Japanese Patent Publication No. 159489/1983. The reaction can be carried out in an acetic acid, dichloromethane or like inert organic solvent at about −20° to about 30° C. in the presence of an electrophilic halogenating agent such as chlorine, bromine or iodine, or N-chlorosuccinimide, N-bromosuccinimide, N-iodosuccinimide or the like. When the compound [5] is fluorinated, preferably the compound is metallated using a strong base such as n-butyllithium and the metallated compound is fluorinated with perchloroyl fluoride or like fluorinating agent.

The 3-halogeno-2,3-diphenylacrylaldehyde derivatives [1] of the invention per se has an excellent activity of lowering the concentration of lipids and is thus useful for treating or preventing, e.g., hypercholesterolemia, hypertriglyceridemia, hyperphospholipidemia, hyper-free fatty acidemia and like hyperlipidemia.

The present invention also provides a pharmaceutical composition for treating hyperlipidemia, the composition containing an effective amount of the derivative of the present invention and a method for treating and preventing hyperlipidemia by administration of the composition to the patients.

Generally, the composition for treating hyperlipidemia of the invention is prepared in the form of a pharmaceutical preparation comprising the foregoing compounds useful as an active ingredient in combination with a pharmaceutically acceptable carrier therefor. Examples of such carrier are conventional diluents and excipients such as fillers, extenders, binders, wetting agents, disintegrating agents, surfactants, lubricants. These carriers are suitably selected depending on the administration unit form of the preparation.

Administration unit forms of the medicinal preparation of the invention can be selected from a wide variety of those so as to meet the therapeutical purpose. Typical examples of such form are tablets, pills, powders, solutions, suspensions, emulsions, granules, capsules, suppositories, injections (solutions, suspensions and others) and the like. Carriers useful for shaping the medicinal preparation into tablets are lactose, purified sugar, sodium chloride, glucose, urea, starch, calcium carbonate, kaolin, crystalline cellulose, silicic acid, potassium phosphate and like excipients; water, ethanol, propanol, simple syrup, glucose solutions, starch solutions, gelatin solutions, carboxymethyl cellulose, hydroxypropyl cellulose, methyl cellulose, polyvinylpyrrolidone and like binders; sodium carboxymethyl cellulose, calcium carboxymethyl cellulose, low-substituted hydroxypropyl cellulose, dried starch, sodium alginate, agar powder, laminaran powder, sodium bicarbonate, calcium carbonate and like disintegrating agents; a fatty acid ester of polyoxyethylene sorbitan, sodium lauryl sulfate, monoglyceride stearate and like surfactants; purified sugar, stearin, cacao butter, hydrogenated oils and like disintegration inhibitors; quaternary ammonium base, sodium lauryl sulfate and like absorption accelerators; glycerol, starch and like wetting agents; starch, lactose, kaolin, bentonite, colloidal silicic acid and like absorbents; purified talc, stearic acid salts, boric acid powder, poly(ethylene glycol) and like lubricants, etc. If necessary, the tablets can be further coated with a usual coating film to obtain coated tablets, for example sugar-coated tablets, gelatin-coated tablets, enteric-coated tablets, film-coated tablets, or double-layer tablets, multilayered tablets, etc. Carriers useful for shaping the preparation into pills are glucose, lactose, starch, cacao butter, hydrogenated vegetable oils, kaolin, talc and like excipients; gum arabic powder, tragacanth gum powder, gelatin, ethanol and like binders; laminaran, agar powder and like disintegrating agents, etc. Carriers for shaping the preparation into suppositories are poly(ethylene glycol), cacao butter, higher alcohols, esters of higher alcohols, gelatin, semisynthetic glyceride and the like. Capsules are usually formed by the conventional method as by mixing the compound of the invention as an active ingredient with the carriers as exemplified above, and encapsulating the mixture into hardgelatin capsules, soft-gelatin capsules or the like. In forming injectable solutions, emulsions and suspensions, they are sterilized and preferably made isotonic to the blood. Diluents useful for this purpose are, for example, water, ethanol, polyethylene glycol, propylene glycol, ethoxylated isostearyl alcohol, polyoxylated isostearyl alcohol, polyoxyethylene sorbitan fatty acid esters and the like. In preparing isotonic solutions, sodium chloride, glucose or glycerol may be added in an amount sufficient to make the solution isotonic. The pharmaceutical composition of the invention may contain a common solubilizer, buffer solutions, analgesic agents or the like. When required, the preparation of the invention may further contain colorants, preservatives, flavoring agents, sweetening agents and other medicaments.

Although the amount of the compound of the formula [1] as an active ingredient is not specifically restricted and can be suitably selected from a wide range, it is preferred that about 1 to about 85 wt % of the compound be incorporated into the medicinal preparation.

The administration mode of the medicinal preparation according to the invention is not specifically limited and is suitably determined depending on the administration form for the preparation, the patient's age, sex and other conditions, severity of symptoms, etc. For example, tablets, pills, solutions, suspensions, emulsions, granules and capsules are orally administered, and injections are intravenously administered singly or in the form of a mixture with a common injectable auxiliary such as a glucose solution, an amino acid solutions or the like. If necessary, injections are singly administered intramuscularly, intracutaneously, subcutaneously or intraperitoneally. Suppositories are administered into rectum.

A suitable dosage of the medicinal preparation of the invention may be selected depending on the mode of administration, patient's age, sex and other conditions, and severity of the symptoms. The preparation of the invention is usually administered in an amount of about 0.5 to about 100 mg/kg of the body weight/day, calculated as the compound of the invention (active ingredient) and can be applied in 2 to 4 divided doses per day.

The derivatives of the invention can be in the form of E- and/or Z-geometrical isomers which are included in the present invention.

The present invention will be described below in more detail with reference to the following Examples illustrating the preparation of the derivatives of the invention.

EXAMPLE 1

Preparation of
3-chloro-3-(4-fluorophenyl)-2-(4-methylsulfonylphenyl)acrylaldehyde Step 1

First, a mixture of 110 g (0.51 mole) of 4-methylsulfonylphenylacetic acid and 110 ml (1.51 moles) of thionyl chloride was heated at 90° C. for 2 hours. After completion of the reaction, an excess of thionyl chloride was distilled off under reduced pressure, giving about 120 g of 4-methylsulfonylphenylacetyl chloride as a light brown solid. The solid thus obtained was subjected to the subsequent reaction without isolation and purification.

Thereafter 102 g (0.765 mole) of anhydrous aluminum chloride was suspended in 200 ml of fluorobenzene. To the suspension was added dropwise a suspension of 120 g of the 4-methylsulfonylphenylacetyl chloride obtained above in 200 ml of fluorobenzene at a temperature of 0° to 3° C. The reaction vessel used was rinsed with 30 ml of fluorobenzene and the mixture was stirred at 20° C. for 4 hours. The reaction mixture was gradually poured into a mixture of ice water and hydrochloric acid and left to stand overnight, giving gummy solids. The solids were collected by filtration. The organic layer was separated from the filtrate and subjected to distillation under reduced pressure to recover 200 ml (52%) of fluorobenzene. The gummy solids were dissolved in dichloromethane, washed sequentially with water, a 5% aqueous solution of sodium bicarbonate and a saturated saline solution and dried over magnesium sulfate. The dichloromethane was distilled off and the resulting crystals were washed with diethyl ether, giving 77 g (51%) of 1-(4-fluorophenyl)-2-(4-methylsulfonylphenyl)ethanone as pale yellow solids.

Melting point: 173°–176° C.

The solids obtained were purified by silica gel column chromatography (eluent, dichloromethane-ethyl acetate).

Melting point: 181°–183° C.

$^1$H-NMR (CDCl$_3$): δ, 8.05 (2H, dd, J=8.7, 5.4), 7.92 (2H, d, J=8.3), 7.46 (2H, d, J=8.3), 7.17 (2H, dd, J=8.4, 8.4), 4.38 (2H, s), 3.06 (3H, s).

A 7.4 g (7%) quantity of 4-methylsulfonylphenylacetic acid was recovered from the washings containing the aqueous solution of sodium bicarbonate used hereinabove.

Step 2

A 54 g quantity (0.18 mole) of 1-(4-fluorophenyl)-2-(4-methylsulfonylphenyl)ethanone was suspended in a mixture of 500 ml of chloroform and 57 ml (0.74 mole) of N,N-dimethylformamide. To the suspension was added dropwise with stirring 60 ml (0.64 mole) of phosphorus oxychloride over a period of 30 minutes with cooling in an ice-saline solution bath. After the addition, the resulting mixture was further stirred at 20° C. for 2 hours and refluxed with heating for 18 hours. After being cooled to room temperature, the reaction mixture was poured into ice water and extracted with chloroform. The organic layer was washed sequentially with water and a saturated saline solution, dried over magnesium sulfate and concentrated. The resulting crystals were washed with a 1:2 mixture of diethyl ether and n-hexane, giving 54 g (86%) of the desired product in the form of a mixture of E- and Z-isomers as light brown solids.

$^1$H-NMR (CDCl$_3$): δ, [10.55 (s), 9.66 (s), 1H], [8.05–6.87 (m), 8H], [3.11 (s), 3.03 (s), 3H].

The product was further purified by silica gel column chromatography (eluent, dichloromethane-ethyl acetate), giving an E-isomer.

Melting point: 149°–150° C.

$^1$H-NMR (CDCl$_3$): δ, 9.66 (1H, s), 8.03 (2H, d, J=8.0), 7.60 (2H, dd, J=8.3, 5.0), 7.50 (2H, d, J=8.0), 7.23 (2H, dd, J=8.3, 8.3), 3.11 (3H, s).

EXAMPLE 2

Preparation of 3-chloro-3-(4-fluorophenyl)-2-(4-methylthiophenyl)acrylaldehyde

Step 1

A mixture of 158 g (0.87 mole) of 4-methylthiophenylacetic acid and 150 ml (2 moles) of thionyl chloride was heated at 90° C. for 2 hours. After completion of the reaction, an excess of thionyl chloride was distilled off under reduced pressure, giving about 120 g of 4-methylthiophenylacetyl chloride as a black oily product. The oily product thus obtained was subjected to the subsequent reaction without isolation and purification.

Thereafter 174 g (1.3 moles) of anhydrous aluminum chloride was suspended in 600 ml of fluorobenzene. To the suspension was added dropwise a solution of 175 g of 4-methylthiophenylacetyl chloride obtained in the same manner as above in 120 ml of fluorobenzene at a temperature of 0° to 3° C. The resulting mixture was stirred at 20° C. for 3.5 hours. Then the reaction mixture was gradually poured into a mixture of ice water and hydrochloric acid, followed by extraction with dichloromethane. The dichloromethane layer was washed sequentially with a 5% aqueous solution of sodium bicarbonate and a saturated saline solution and dried over magnesium sulfate. The dichloromethane was distilled off and the resulting crystals were dissolved in 300 ml of a 2:1 mixture of ethyl acetate and isopropyl ether with heating. Ten grams of activated carbon was added and the solution was filtered. The separated crystals were collected by filtration, giving 92 g (40%) of 1-(4-fluorophenyl)-2-(4-methylthiophenyl)ethanone as pale yellow solids.

Melting point: 135°-136° C.

The solids were further purified by silica gel column chromatography (eluent, dichloromethane).

Melting point: 140°-141° C.

$^1$H-NMR (CDCl$_3$): δ, 8.03 (2H, dd, J=8.7, 2.0), 7.26-7.09 (6H, m) 4.21 (2H, s), 2.46 (3H, s).

Step 2

A 48 g quantity (0.18 mole) of 1-(4-fluorophenyl)-2-(4-methylthiophenyl)-ethanone was suspended in a mixture of 500 ml of chloroform and 57 ml (0.74 mole) of N,N-dimethylformamide. To the suspension was added dropwise 60 ml (0.64 mole) of phosphorus oxychloride with stirring over a period of 30 minutes with cooling in an ice-saline solution bath. After the addition, the resulting mixture was further stirred at 20° C. for 2 hours and refluxed with heating for 18 hours. After being cooled to room temperature, the reaction mixture was added to ice water and then extracted with chloroform. The organic layer was washed with water and a saturated saline solution in this sequence and dried over magnesium sulfate, followed by concentration under reduced pressure. The resulting crystals were washed with a 1:3 mixture of diethyl ether and n-hexane, giving 53 g (94%) of the desired product in the form of a mixture of E- and Z-isomers as light brown solids.

$^1$H-NMR (CDCl$_3$): δ, [10.55 (s), 9.64 (s), 1H], 7.56 (1H, dd, J=8.4, 5.2), [6.86-7.33 (m), 7H], [2.51 (s), 2.43 (s), 3H].

The product was subjected to silica gel column chromatography (eluent, ethyl acetate-n-hexane) for purification, giving an E-isomer.

Melting point: 131°-133° C.

$^1$H-NMR (CDCl$_3$): δ, 9.64 (1H, s), 7.56 (2H, dd, J=8.4, 5.2), 7.15-7.33 (6H, m), 2.51 (3H, s)

Given below is an example illustrative of a pharmacological test carried out using the derivatives of the present invention.

PHARMACOLOGICAL TEST EXAMPLE 1

A suspension of a test compound in 0.5% carboxymethyl cellulose (CMC) was orally administered to 7-week old Wista rats (7 rats in each group) for 5 consecutive days (100 mg/5 ml/kg/day).

The blood of each rat was collected four hours after the final administration and the amount of triglyceride in the plasma was measured with Triglyceride G-Test Wako (product of Wako Pure Chemicals Co., Ltd.). On the other hand, a control group to which only 0.5% CMC was given beforehand was subjected to the same pharmacological test as above.

Table 1 shows the results.

TABLE 1

| Test compound | Amount of triglyceride in plasma (mg/dl) (mean ± S.D.) |
|---|---|
| Compound of Ex. 1 | 128 ± 11* |
| Compound of Ex. 2 | 111 ± 23** |
| Control | 161 ± 31 |

In Table 1, the symbols "*" and "**" stand for $p<0.05$ and $p<0.01$, respectively as compared with the control group.

Table 1 reveals that the compounds of the present invention exhibit an outstanding activity of decreasing the amount of triglyceride in the plasma and are useful as a medicament for treating hyperlipidemia.

Given below are Preparation Examples using the compounds of the present invention.

PREPARATION EXAMPLE 1

| | |
|---|---|
| Compound of Ex. 1 | 250 g |
| Crystalline cellulose (Japanese Pharmacopeia grade) | 30 g |
| Corn starch (Japanese Pharmacopeia grade) | 17 g |
| Talc (Japanese Pharmacopeia grade) | 2 g |
| Magnesium stearate (Japanese Pharmacopeia grade) | 1 g |
| Total amount | 300 g |

The above ingredients were pulverized into fine particles and fully mixed together to form a homogeneous mixture. The mixture was filled into gelatin capsules for oral administration having a predetermined size, giving desired encapsulated preparations (1000 capsules).

PREPARATION EXAMPLE 2

| | |
|---|---|
| Compound of Ex. 2 | 100 g |
| Crystalline cellulose (trade name: "Avicel pH101", product of Asahi Chemical Industry Co., Ltd.) | 40 g |
| Corn starch | 30 g |
| Magnesium stearate | 2 g |
| Total amount | 172 g |
| Hydroxypropyl methyl cellulose (trade name: "TC-5", product of Shin-etsu Chemical Industry Co., Ltd.) | 8.0 g |
| Poly(ethylene glycol)-6000 | 2.4 g |

| -continued | |
|---|---|
| Colorant | 0.6 g |
| Titanium dioxide | 4.0 g |
| Water | 85.0 g |
| Total amount | 100 g |

The compound of Example 2, crystalline cellulose, corn starch and magnesium stearate were mixed together and ground. The mixture was formulated into tablets with use of a sugar-coated punch having a radius of 8 mm. The tablets were coated with a film-forming agent consisting of hydroxypropyl methyl cellulose ("TC-5"), poly(ethylene glycol)-6000, colorant, titanium dioxide and water, giving film-coated tablets (500 tablets) having the foregoing composition.

We claim:

1. A 3-halogeno-2,3-diphenylacrylaldehyde derivative represented by the formula

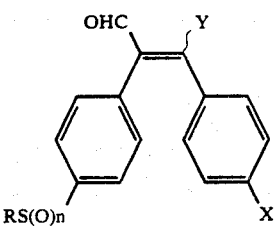

wherein R is an alkyl group having 1 to 6 carbon atoms, X and Y each represent a halogen atom, and n is 0, 1 or 2.

2. A 3-halogeno-2,3-diphenylacrylaldehyde derivative represented by the formula as shown in claim 1 wherein X is a fluorine atom and Y is a chlorine atom.

3. A process for preparing the 3-halogeno-2,3-diphenylacrylaldehyde derivative as defined in claim 1, the process comprising the steps of reacting a phenylacetyl halide derivative represented by the formula

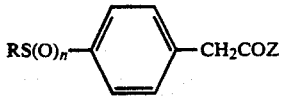

wherein R and n are as defined above, and Z is a halogen atom, with a halogenobenzene derivative represented by the formula

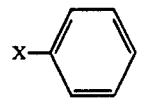

wherein X is as defined above in the presence of a Lewis acid to obtain a desoxybenzoin derivative represented by the formula

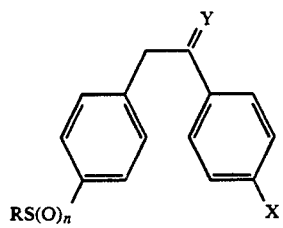

wherein R, X and n are as defined above, and treating the desoxybenzoin derivative with N,N-disubstituted formamide and an oxyhalide.

4. A pharmaceutical composition for preventing and treating hyperlipidemia which comprises a pharmacologically effective amount of a 3-halogeno-2,3-diphenylacrylaldehyde derivative represented by the formula

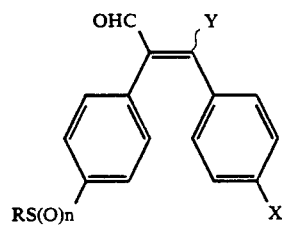

wherein R is an alkyl group having 1 to 6 carbon atoms, X and Y each represent a halogen atom, and n is 0, 1 or 2.

5. A method for preventing or treating hyperlipidemia comprising administering a pharmacologically effective amount of a 3-halogeno-2,3-diphenylacrylaldehyde derivative represented by the formula

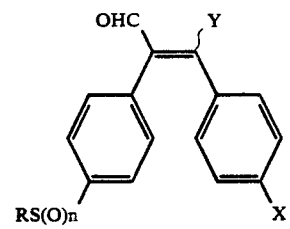

wherein R is an alkyl group having 1 to 6 carbon atoms, X and Y each represent a halogen atom, and n is 0, 1 or 2.

* * * * *

UNITED STATES PATENT AND TRADEMARK OFFICE
CERTIFICATE OF CORRECTION

PATENT NO. : 5,082,974
DATED : January 21, 1992
INVENTOR(S) : Kinji HASHIMOTO et al It is certified that error appears in the above-indentified patent and that said Letters Patent is hereby corrected as shown below:

On the Title page, item [54], last line, "HYPERLIPIDEMI" should read -- HYPERLIPIDEMIA --.

On the Title page, item [73], "Pharaceutical" should read -- Pharmaceutical --.

Col. 1, line 6, "Hyperlipidemi" should read --Hyperlipidemia--.

Signed and Sealed this

Eighth Day of June, 1993

Attest:

MICHAEL K. KIRK

*Attesting Officer*  Acting Commissioner of Patents and Trademarks

UNITED STATES PATENT AND TRADEMARK OFFICE
CERTIFICATE OF CORRECTION

PATENT NO. : 5,082,974
DATED      : January 21, 1992
INVENTOR(S): Kinji Hashimoto et al It is certified that error appears in the above-indentified patent and that said Letters Patent is hereby corrected as shown below:

In Column 12, lines 10 - 20, the formula should read:

-- 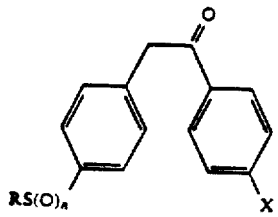 --

Signed and Sealed this

First Day of March, 1994

*Attest:*

BRUCE LEHMAN

*Attesting Officer*   Commissioner of Patents and Trademarks